United States Patent [19]

Ames et al.

[11] Patent Number: 6,043,505
[45] Date of Patent: Mar. 28, 2000

[54] DEVICE AND METHOD FOR MONITORING FLUIDS WITH A DETECTION OF CROSS SECTIONAL SHAPE OF TRANSMITTED BEAM

[76] Inventors: Donald P. Ames, 914 Black Twig La., St. Louis, Mo. 63122; Daniel L. Rode, Nine Prado, St. Louis, Mo. 63124

[21] Appl. No.: 09/130,330

[22] Filed: Aug. 6, 1998

[51] Int. Cl.$^7$ .................................................. G01N 15/06
[52] U.S. Cl. ........................... 250/577; 250/225; 356/70; 73/293
[58] Field of Search .................................... 250/577, 225, 250/573, 574, 904, 902; 356/70, 436, 440, 351, 364; 430/619, 603, 612; 73/293, 290 R

[56] References Cited

U.S. PATENT DOCUMENTS

| | | | |
|---|---|---|---|
| 3,713,743 | 1/1973 | Simms | 356/208 |
| 3,790,279 | 2/1974 | Skala | 356/70 |
| 3,876,307 | 4/1975 | Skala | 356/104 |
| 4,570,069 | 2/1986 | Gager | 250/343 |
| 4,699,509 | 10/1987 | Kamiya et al. | 356/70 |
| 4,786,171 | 11/1988 | LeFebre et al. | 356/326 |
| 4,857,894 | 8/1989 | Dahl | 250/577 |
| 5,021,665 | 6/1991 | Ames | 250/357.1 |
| 5,076,397 | 12/1991 | Yamada | 184/108 |
| 5,296,843 | 3/1994 | Wohlstein et al. | 340/603 |
| 5,739,916 | 4/1998 | Englehaupt | 356/414 |

FOREIGN PATENT DOCUMENTS

| | | |
|---|---|---|
| 8-221684 | 2/1995 | Japan . |
| 2280265 | 7/1993 | United Kingdom . |

OTHER PUBLICATIONS

Lee, Han–Sheng, et al., "In situ monitoring of high–temperature degraded engine oil condition with microsensors," *Sensors and Actuators B,* 20 (1994), pp. 49–53, (Month Unknown).

Ma, Hanqing, "The Analysis Of Used Engine Oils And An Investigation Into Correlation Of Performance Deterioration In Service," *Mechanical Properties/Materials Design,* B. Wu editor, Elsevier Science Publishers B.V., 1991, pp. 537–542, (Month Unknown).

Wang, Simon S., et al., "The development of in situ electrochemical oil–condition sensors," *Sensors and Actuators B,* 17 (1994), pp. 179–185, (Month Unknown).

*Primary Examiner*—Que T. Le
*Attorney, Agent, or Firm*—Senniger, Powers, Leavitt & Roedel

[57] ABSTRACT

A fluid monitor determines the quality, intensity and/or level of a fluid by transmitting a beam of light through the fluid and evaluating any changes to the shape of the beam as a result of being transmitted through the fluid. The monitor includes a light source and a lens which generate an incident beam of light having a predefined cross sectional shape. The beam is transmitted through a volume of the fluid, which modifies the shape of the beam as a function of the fluid quality, intensity and/or level. The beam can be polarized before being transmitted through the fluid or after beam transmission. The polarized beam is directed to a detector which evaluates the horizontal and vertical components of the beam and provides a shape signal to a detection circuit. The detection circuit processes the shape signal received from the detector to determine the quality, intensity and/or level of the fluid based on any variations from the predefined shape of the incident beam. The detection circuit outputs a signal to a display unit indicating the quality, intensity and/or level of the fluid. The detection circuit may also actuate an alarm if the quality, intensity and/or level of the fluid is below a preselected minimum value.

35 Claims, 6 Drawing Sheets

DEVICE AND METHOD FOR MONITORING FLUIDS WITH A DETECTION OF CROSS SECTIONAL SHAPE OF TRANSMITTED BEAM

BACKGROUND OF THE INVENTION

The present invention relates generally to a device and method for monitoring fluids and, in particular, to a device and method for determining the quality, intensity and/or level of a fluid by evaluating the shape of a polarized beam of light.

Electromagnetic radiation (e.g., ultraviolet, visible or infrared light) can be used to non-destructively characterize the chemical composition of gases, fluids and solids through absorption or scattering. "Optical absorption" involves the conversion of energy from the electromagnetic field into excitation of the electron energy levels of the elemental atoms or compounds present. "Light scattering" refers to the redirection of part of the light beam along paths different from that of the original beam (e.g., Rayleigh, Rayleigh-Brillouin and Mie scattering).

In the context of the present invention, the term fluid "intensity" refers to the degree of or magnitude of contamination resulting from the presence of foreign particles and/or liquid dispersions in the fluid. By contrast, the term fluid "quality" refers to the degree of degradation as a result of fluid usage. The term fluid "parameter" refers broadly to one or more variables associated with the fluid, such as intensity, quality and/or level.

With respect to lubricating oils and many other fluids, increased contamination or degradation of the fluid will result in increased absorption and scattering. Therefore, if a beam of light is transmitted through fresh oil, the shape of the transmitted beam will be isotropic. However, if the same beam of light is transmitted through either degraded oil or contaminated oil, the shape of the transmitted beam will be anisotropic. In fact, the shape of the transmitted beam becomes more anisotropic as the contamination and/or degradation increases. Thus, the intensity and the quality of the fluid may be determined by evaluating the shape of the transmitted beam.

There are a number of known applications for fluid monitors. For example, the operator of an automobile periodically monitors oil quality and level or risks costly damage to the engine. The degradation of engine oil in passenger automobiles and trucks depends on factors such as the initial oil quality, engine type, engine condition, engine load, oil operating temperature, usage time, length and distance of driving, oil consumption and individual driving habits. A general guideline for oil change intervals suitable for all drivers is difficult to establish.

One prior art device for monitoring the oil level in an automobile engine is a dipstick. A conventional dipstick does not measure oil quality or intensity, and it must be manually removed to determine the level of the oil. While electronic dipsticks are now available which allow drivers to monitor the oil level without physically removing the dipstick, electronic dipsticks do not measure oil quality or intensity.

An optical oil monitor is disclosed in U.S. Pat. No. 3,876,307 to Skala. This monitor (i) measures degradation in oil by passing light through an oil sample and picking up the light that is scattered at 90 degrees by the molecules and particles and (ii) measures chemical breakdown by the attenuation of the light passing substantially straight through the oil. It has been found that measuring degradation in oil based on the amount of light scattered at 90 degrees is not reliable because the highest level of degradation that the monitor can detect is still below the degradation level at which the oil should be replaced. In other words, the monitor becomes ineffective well before the oil must be replaced.

Another known oil level monitor, which is described in U.S. Pat. No. 5,021,665 to Ames, determines the fluid level in a reservoir by evaluating the intensity of fluorescent radiation emitted by the fluid. While this device adequately monitors the oil level, it is not acceptable for determining oil quality in an automobile. As with the Skala monitor, it has been found that the oil quality may still be acceptable for some time after the oil has absorbed the radiation to the point that no more radiation can be detected by the monitor.

Other existing methods for measuring oil quality and intensity are not practical for applications such as the operation of an automobile. Such methods would require the automobile operator to periodically remove a sample of the oil and transport it to a location equipped for testing the oil quality and intensity. Such methods are inefficient from both a time and a cost standpoint and are not capable of evaluating the fluid in situ.

Accordingly, there exists a need for a practical and cost-effective means for monitoring the quality of a fluid to eliminate unnecessary maintenance and to reduce costly repairs resulting from the use of degraded fluid. There is also a need for a practical and cost-effective means for monitoring the intensity of a fluid to detect the presence of contaminants as soon as possible so that the source of the contamination can be identified. Further, there is a need for a fluid level monitor which is also capable of effectively monitoring the quality and/or intensity of a fluid.

SUMMARY OF THE INVENTION

The present invention overcomes the prior art problems noted above by providing a device and method for determining the quality, intensity and/or level of a fluid in situ by evaluating the shape of a beam of light transmitted through the fluid. The term "incident beam" is used herein to refer to a beam of light before it passes through the fluid, and the term "transmitted beam" is used herein to refer to a beam of light after it passes through the fluid.

It is an object of the present invention to provide a device and method for monitoring the quality of a fluid by evaluating the shape of a beam of light transmitted through the fluid to effectively determine when the fluid should be replaced.

It is another object of the present invention to provide a device and method for monitoring the intensity of a fluid by evaluating the shape of a beam of light transmitted through the fluid to effectively detect the presence of a foreign solid, liquid or gas in the fluid.

It is yet another object of the present invention to provide a device and method for monitoring the level of a fluid by evaluating the shape of a beam of light transmitted through the fluid to effectively determine when additional fluid should be added.

It is a further object of the present invention to provide a device and method for in situ monitoring of the quality, intensity and/or level of a fluid such as engine oil.

It is still a further object of the present invention to provide a fluid monitor having a detector for receiving a beam of light transmitted through the fluid and producing a shape signal having a vertical component and a horizontal component to effectively determine the fluid quality, intensity and/or level.

Another object of the present invention is to provide a fluid monitor having a detection circuit for comparing the shape signal to the predefined shape of the incident beam to effectively determine the quality, intensity and/or level of the fluid.

Still another object of the present invention is to provide a device and method for monitoring a fluid by continuously evaluating the shape of the transmitted beam to indicate any time-dependent fluctuations of the fluid quality, intensity and/or level.

These and other related objects of the present invention will become readily apparent upon further review of the specification and drawings. To accomplish the objects of the present invention, a fluid monitoring device is provided which includes a light source, a beam conditioner for directing a beam of light having a predefined cross sectional shape through the fluid, a detector for receiving the transmitted beam and for providing a shape signal representative of the cross sectional shape of the transmitted beam, an optical polarizer, and a circuit for receiving the shape signal and providing a signal indicative of the quality, intensity and/or level of the fluid.

In another aspect, the objects and advantages of the present invention may be achieved by a method for monitoring the value of a parameter associated with a fluid comprising the steps of providing light, conditioning the light into a beam, transmitting the beam through the fluid, detecting the transmitted beam, generating a shape signal corresponding to the transmitted beam, analyzing the shape signal and generating an output signal indicating the value of the parameter.

BRIEF DESCRIPTION OF THE DRAWINGS

So that the manner in which the above-recited features, advantages and objects of the present invention are attained and can be understood in detail, a more particular description of the invention, briefly summarized above, may be had by reference to the embodiments thereof which are illustrated in the appended drawings.

It is noted, however, that the appended drawings illustrate only exemplary embodiments of this invention and are therefore not to be considered limiting of its scope, for the invention may admit to other equally effective embodiments. Reference the appended drawings, wherein.

DESCRIPTION OF THE PREFERRED EMBODIMENTS

Figure 1:
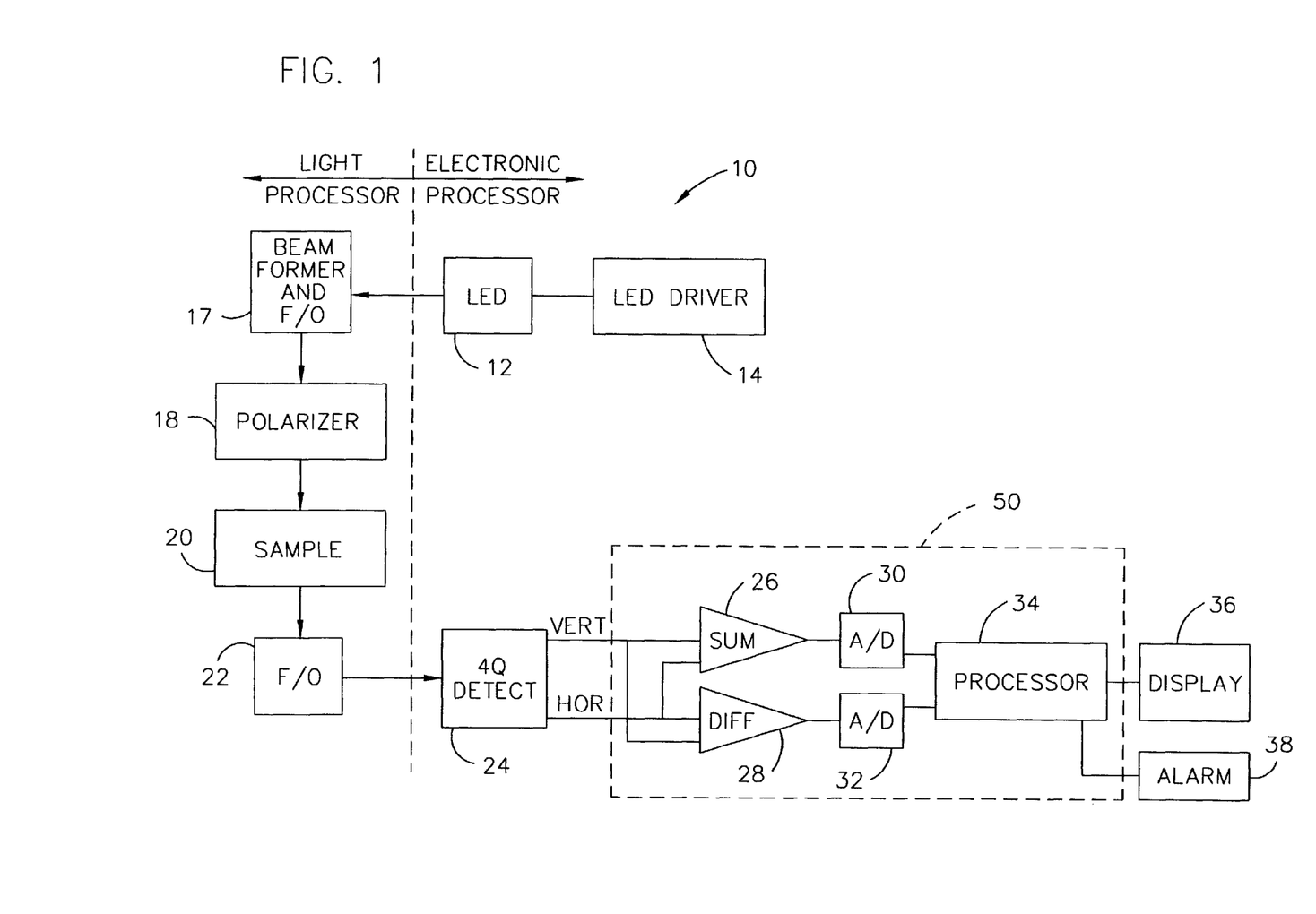
FIG. 1 is a block diagram of one preferred embodiment of a monitor according to the invention.
Figure 2:
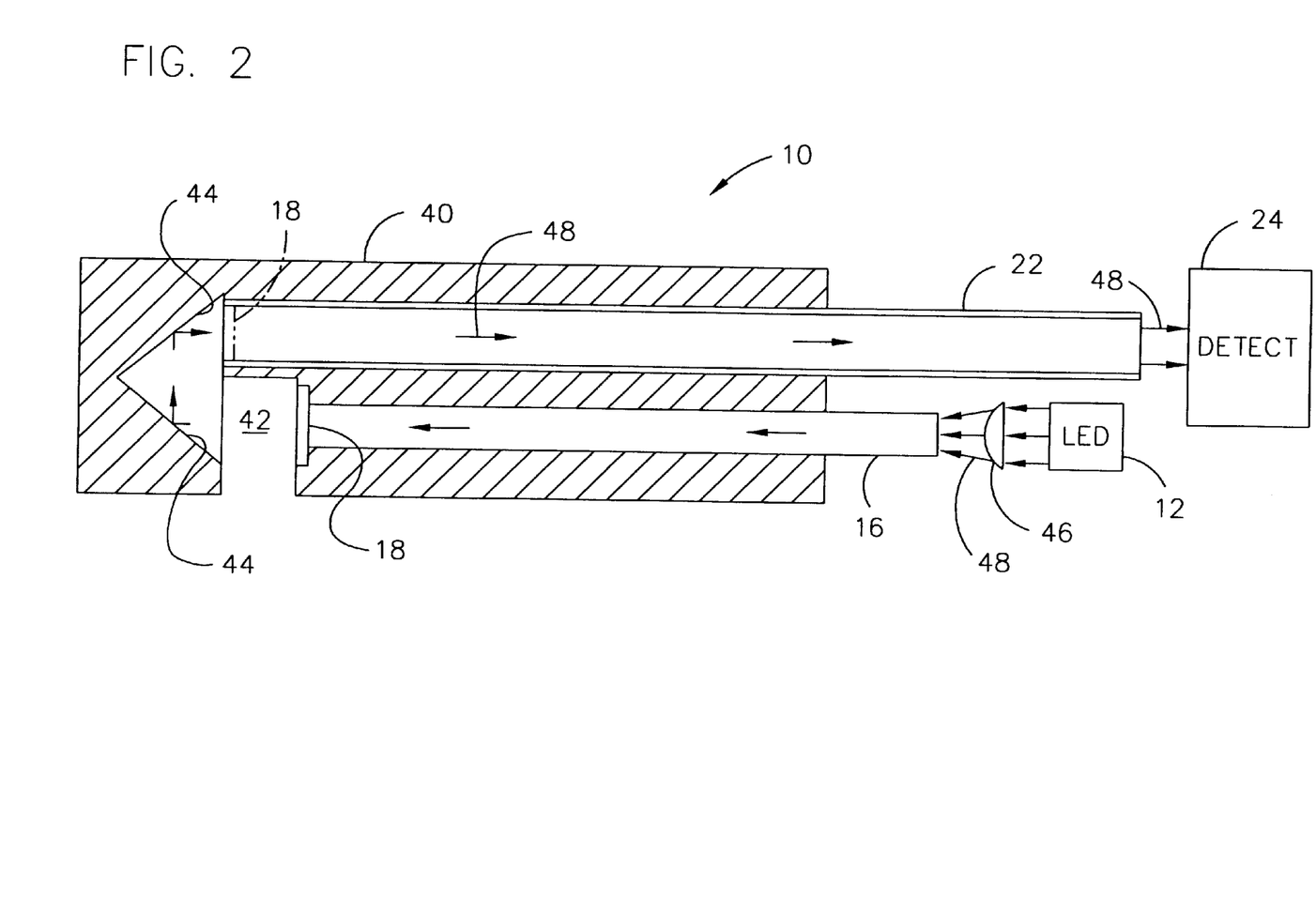
FIG. 2 is a schematic diagram in longitudinal cross section illustrating the light path of the monitor according to the invention.

Referring to the drawings in greater detail, and initially to FIGS. 1 and 2, the fluid monitor of the present invention is designated generally by reference numeral 10. Monitor 10, shown in block diagram form in FIG. 1, comprises a light processor and an electronic processor. The electronic processor includes a light emitting diode (LED) 12 and LED driver 14. The light processor receives light from light source 12 through a beam former and fiber optic strand 17, which is coupled with an optical polarizer 18 and a fluid sample 20. A fiber optic bundle 22 is disposed between fluid sample 20 and a detector 24 so that the bundle directs the beam back to the electronic processor. A second polarizer 18 (shown in phantom lines in FIG. 2) may be disposed transversely across bundle 22 either in lieu of or in addition to the polarizer shown between light source 12 and fluid sample 20.

Four quadrant detector 24 has north, south, east and west quadrants for measuring the amount of light received in each quadrant via link 22. The north and south quadrants are referred to as the "vertical" quadrants, and the east and west quadrants are referred to as the "horizontal" quadrants.

The detector 24 produces a vertical signal indicating the total amount of light received in the vertical quadrants and a horizontal signal indicating the total amount of light received in the horizontal quadrants. These vertical and horizontal signals are input to both a summer 26 and a differentiator 28, and the outputs of the summer and differentiator are input to analog-to-digital converters 30, 32 and then to a processor 34. The use of converters 30, 32 is optional, and the outputs of the summer and differentiator may be input directly to the processor 34. The processor 34 divides the difference signal by the sum signal and outputs a display signal to display unit 36. The processor 34 is also coupled with an alarm 38 for sending an alarm signal indicating, for example, that the fluid quality is low.

FIG. 2 schematically depicts a preferred embodiment of monitor 10, wherein a fiber optic link 16 and bundle 22 are disposed within an elongated sheath 40. Strand 16 is a single multimode optical fiber which is preferably 600 micrometers in diameter, and bundle 22 is a multiple pixel, multimode optical fiber image guide (such as the IGN-10/13 product sold by Sumitomo Electric Industries, Ltd.). The sheath 40 is constructed to present a cavity 42 intermediate links 16, 22 for accommodating a sample volume of the fluid to be monitored. Although monitor 10 preferably includes fiber optic link 16, bundle 22 and sheath 40, these items are not essential to carrying out the present invention.

The polarizer 18 is located at the end of link 16 adjacent recess 42, and a 3.2 millimeter turning mirror 44 is disposed between the recess and link 22 so that light 48 transmitted through the recess will be reflected through link 22. The polarizer 18 could also be located at the junction of mirror 44 and link 22. In a preferred embodiment, the mirror 44 is a right angle prism or turning cube. The preferred monitor 10 further comprises a plano-convex lens 46 located intermediate LED 12 and conduit 16.

Figure 3:
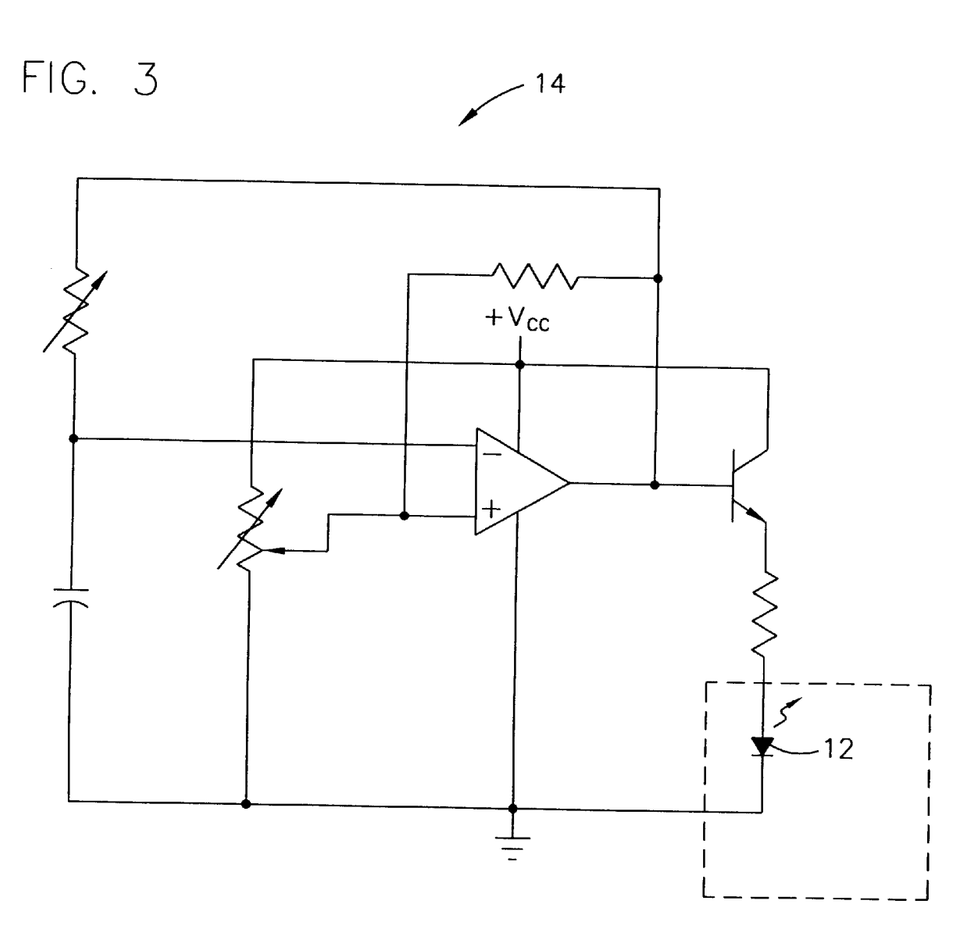
FIG. 3 is a schematic diagram of an LED driver for driving the LED of the monitor according to the invention.

Turning to FIG. 3, a schematic diagram is shown for the LED driver 14 for driving the LED 12 in accordance with a preferred embodiment of the monitor 10. LED 12 is surrounded by broken lines to indicate that it is not located on the circuit board with driver 14. FIG. 3 represents only one of many different circuits contemplated for accomplishing the objects of the present invention. For example, another version of FIG. 3 would be a driver for another type of light source, such as a laser. Those skilled in the art will readily appreciate any number of other modifications that could be made to the driver circuitry.

Figure 4:
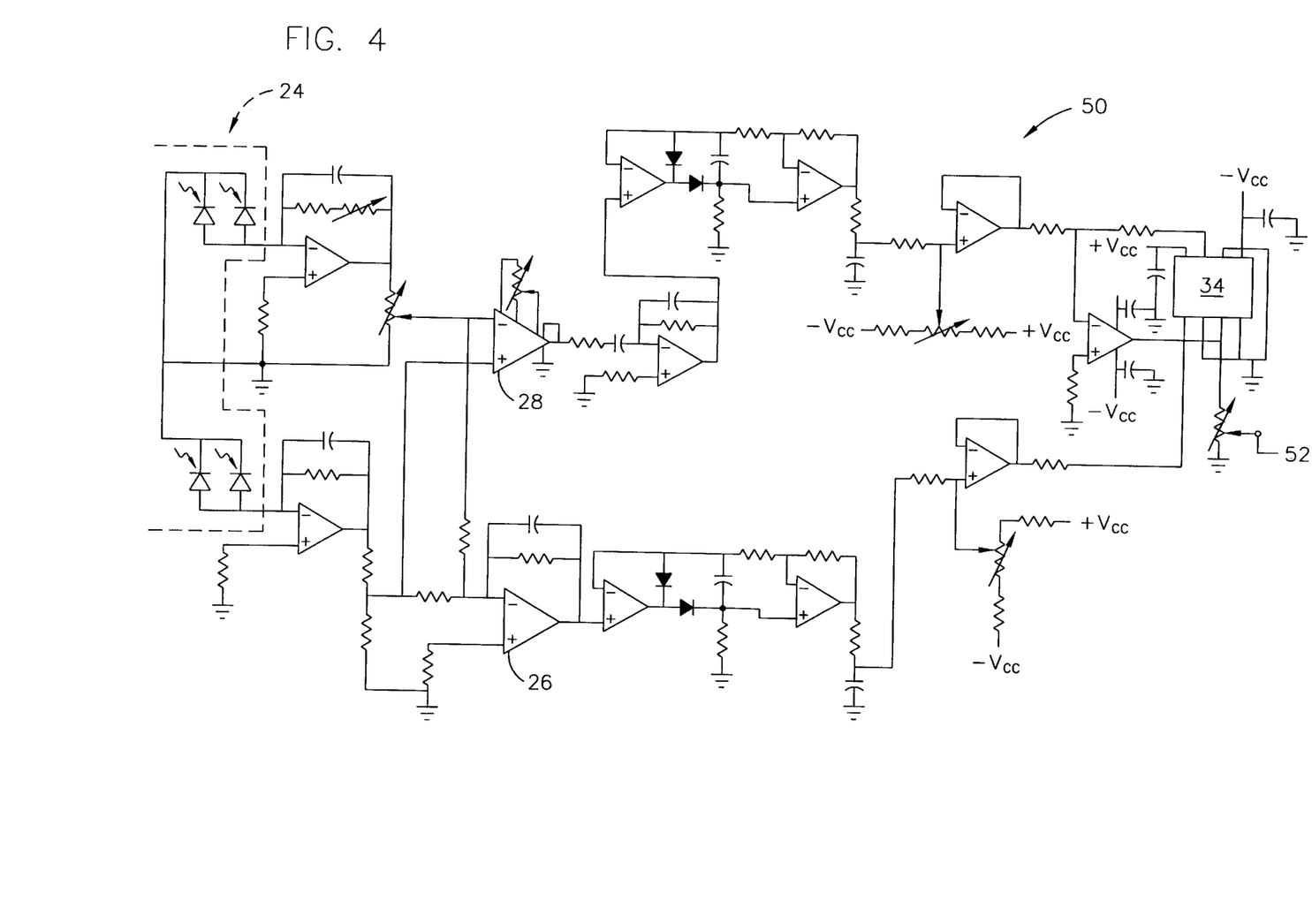
FIG. 4 is a schematic diagram of detection electronics of a monitor according to the invention.

FIG. 4 is a schematic diagram of detection electronics 50 of the monitor 10 according to a preferred embodiment of the invention which does not include analog-to-digital converters. The broken lines in FIG. 4 identify the separation between detector 24 and detection circuit 50. Like FIG. 3, FIG. 4 represents one of many different circuits contemplated for accomplishing the objects of the present invention. Those skilled in the art will readily appreciate any number of modifications that could be made to the detection circuitry.

Figure 5:
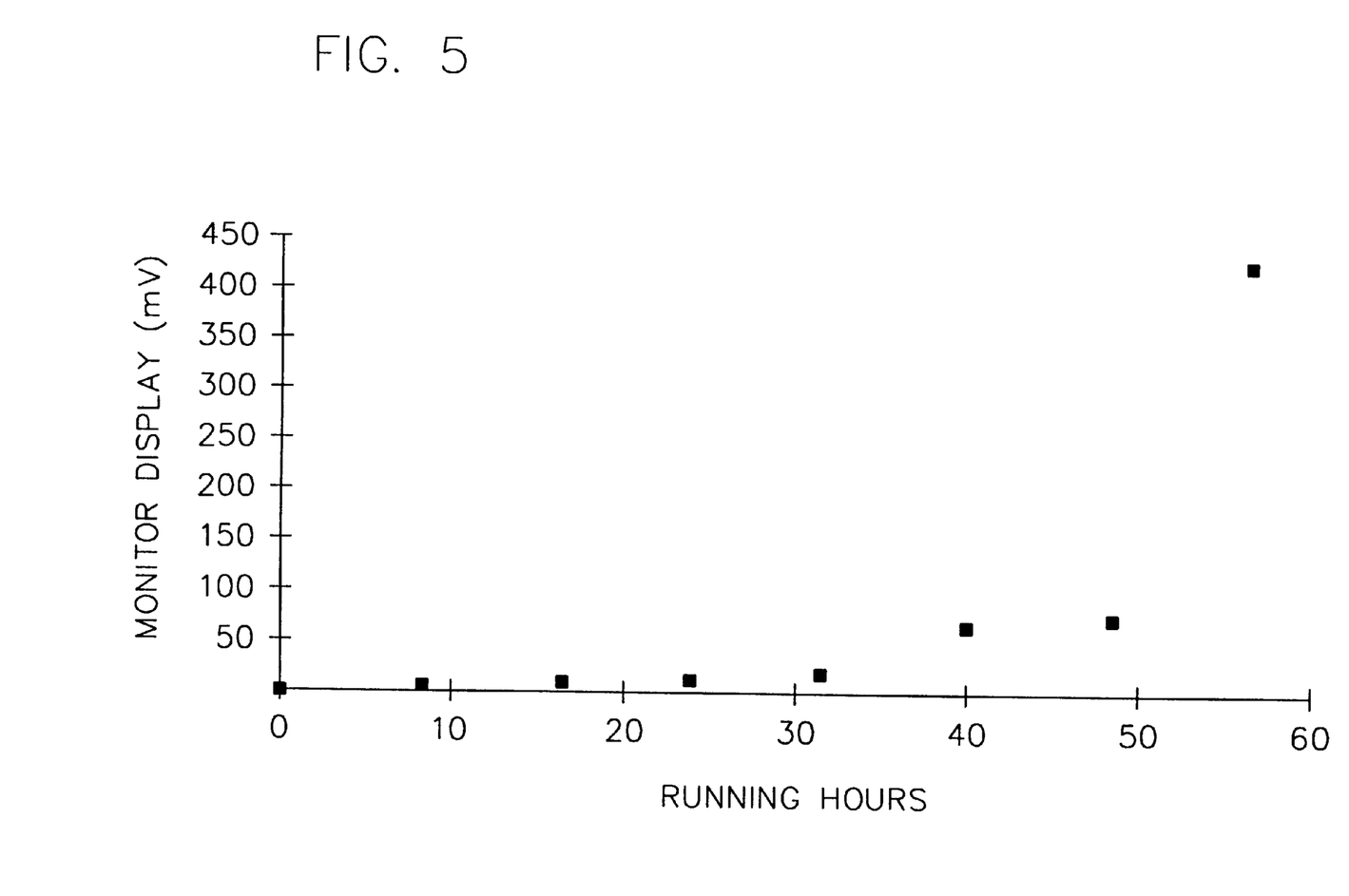
FIG. 5 is a diagram illustrating the relative fluid quality over time based on the display of a monitor according to the invention.
Figure 6:
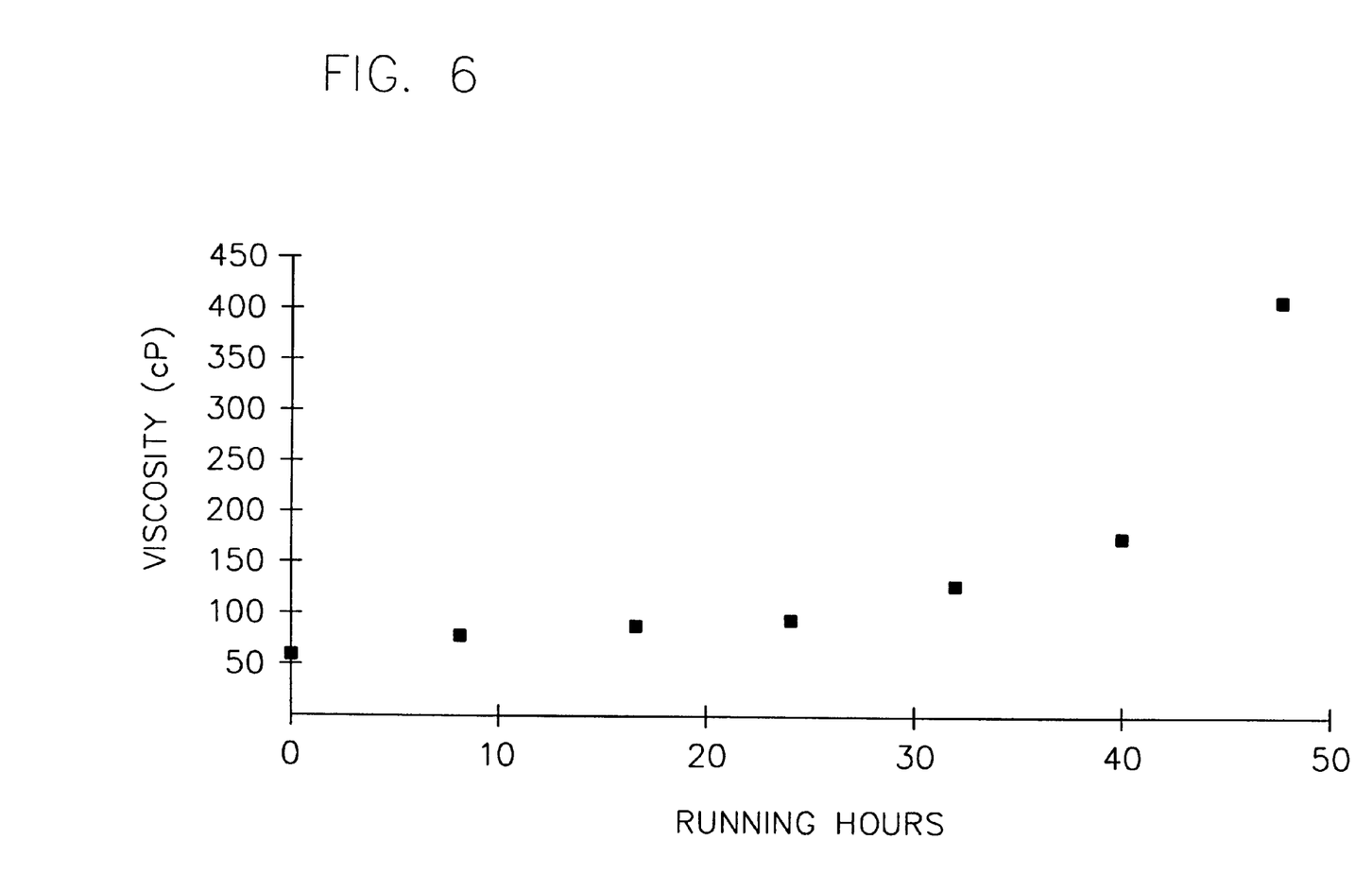
FIG. 6 is a diagram illustrating the relative fluid quality over time based on the viscosity of the fluid.

The data shown in FIGS. 5 and 6 are taken from tests performed on lubricating oil using an engine operating in accordance with the November 1995 report of the American Society for Testing and Materials (ASTM) entitled Standard Test Method for Evaluation of Automotive Engine Oils in the Sequence IIIE, Spark-Ignition Engine, Volume D, pages 5,533 to 5,595. Sequence IIIE is a severe, accelerated test that degrades lubricating oil for 64 hours by continuously operating a 3.8 liter, V6 engine with an 8:1 compression ratio and two-barrel carburetor at a speed of 3,000 rpm, a load of 116 newton-meters, and an oil temperature of 149 degrees Celsius (300 degrees Fahrenheit). An oil sample is removed from the reservoir every eight hours so that eight different oil samples are examined for oil quality.

As illustrated by FIGS. 5 and 6, there is a relationship between the quality of a fluid such as oil and the use of that fluid. The data shown in FIG. 5 were derived using monitor 10 of the present invention. First, the monitor display is calibrated so that the initial reading is zero. Then, the operator selects a range for the monitor display. Although the monitor display is achieved by multiplying the quotient of the difference signal and the sum signal (as determined by a millivolt meter) by 100, the specific value displayed by the monitor is used only for comparison to other displayed values during the same test to ascertain the relative quality of the oil over time. While a range of 0 to 450 was selected in connection with FIG. 5, the operator could have selected another range (e.g., 0 to 200) for the display. In any event, the value of the monitor display is relatively low when the quality of the oil is relatively high (e.g., fresh oil), and the value of the monitor display increases as the oil degrades. A rapid increase in the value or a large value of the monitor display indicates that the oil should be replaced.

The data shown in FIG. 6 are based on viscosity measurements taken from the same oil samples which provided the data for FIG. 5. The relationship between viscosity and oil quality is well known, and the general correspondence of the data in FIGS. 5 and 6 (e.g., a marked decrease in oil quality at 40–50 hours) independently confirms that the monitor of the present invention effectively detects the relative quality of a fluid such as oil.

In operation, circuit 14 (FIG. 3) drives LED 12 to produce an incident beam 48 of light (at near-infrared wavelengths), which is focused on fiber optic strand 16 by lens 46 such that the incident beam 48 has a predefined cross sectional shape or profile (e.g., circular), as shown in FIG. 2. Strand 16 directs the incident beam through polarizer 18, which polarizes the beam 48, and through sample volume 20. One or more polarizers may be located at any point along the fiber optic links 16, 22 so long as polarization occurs prior to detection.

With respect to FIGS. 1 and 2, a preferred embodiment of monitor 10 evaluates the quality, the intensity and the level of the fluid sample. First, with fresh fluid in the reservoir, a reference profile is established by transmitting an incident beam 48 having a predefined shape (e.g., circular) through the fluid sample in the gap 42. The beam is received by the detector 24, and the detection circuit 50 calculates a profile value by dividing the difference between the vertical and horizontal signals by the sum of the horizontal and vertical signals. Because there is typically no contamination or degradation in fresh fluid, there is only a slight change in the shape of the beam resulting in a profile value which is relatively low. Then, the monitor 10 is calibrated by adjusting the profile value for fresh fluid to zero (or another low number) and storing that reference profile value in the memory of the processor 34.

To monitor the quality of the fluid, an incident beam 48 having the same predefined shape (e.g., circular) is transmitted through the fluid sample in the gap 42. As the incident beam is transmitted through sample 20, degradation of the sample volume causes the beam 48 to scatter so that the transmitted beam has a different shape than the incident beam. It has been found that the relative quality of the fluid is proportional to the degree to which the shape of the transmitted beam varies from the predefined shape. Thus, as the fluid becomes more degraded, the profile value will increase with respect to the reference profile for fresh fluid. Further, evaluating the shape of the transmitted beam has been found to be an effective means for detecting relatively high levels of degradation in fluids such as oil. By contrast, prior art monitors measure degradation by the amount of light scattered at 90 degrees and are not reliable because the highest level of degradation that these monitors can detect is still below the degradation level at which the oil should be replaced. Thus, monitor 10 provides an effective and practical means for determining fluid quality.

To monitor fluid intensity, an incident beam 48 having the same predefined shape (e.g., circular) is transmitted through the fluid sample in the gap 42. As the incident beam is transmitted through sample 20, contaminants in the fluid absorb and scatter light from the beam 48. It has been found that the presence of contaminants in the fluid causes the shape of the transmitted beam to vary significantly from the shape of the incident beam. Thus, as the fluid becomes contaminated, the profile value will increase rapidly with respect to the reference profile for fresh fluid. Evaluating the shape of the transmitted beam has been found to be an effective means for early detection of contaminants in fluids such as oil, which may be a sign of engine problems. Thus, monitor 10 provides an effective and practical means for determining fluid intensity.

The monitor 10 is calibrated for detecting the fluid level by placing the body of the monitor within the fluid reservoir so that the gap 42 is located at a minimum threshold level. Next, an incident beam 48 with the same predefined shape (e.g., circular) is transmitted through the gap 42 to determine whether or not there is fluid present at the threshold level. The profile of the transmitted beam will vary from the profile of the incident beam if there is fluid present in the gap at the threshold level. Thus, if the fluid is at or above the threshold level, the transmitted beam will have a profile value at least as high as the predetermined reference profile value for fresh fluid.

On the other hand, the profile of the transmitted beam will not vary from the profile of the incident beam if there is a complete absence of fluid at the threshold level within gap 42. Thus, when the transmitted beam has a profile value below the reference value for fresh fluid, it is an indication that the fluid level is below the threshold level. If the predetermined reference profile value has been set to zero, the profile value for low fluid would be a negative number. Thus, a "fluid present" profile (e.g., a value greater than or equal to zero) and a "no fluid present" profile (e.g., a value less than zero) can be stored in the memory of the processor 34 for purposes of matching an actual profile reading to monitor the fluid level.

Sometimes a fluid meniscus is present in the gap even though the fluid is below the threshold level. By defining a "meniscus" profile having a value which is greater than the "no fluid present" profile value but less than the "fluid present" profile value, the absence of fluid can be distinguished from the presence of a fluid meniscus. These profiles can be stored in the memory of the processor 34.

To monitor the fluid level, the detector 24 receives the transmitted beam 48, and detection circuit 50 calculates the value of the beam profile. Then, the circuit 50 matches that profile value with one of the profiles stored in the memory of the processor 34 to determine the fluid level based on the change in the shape of the beam 48.

Whether monitoring fluid quality, intensity or level, the beam 48 is transmitted through the gap 42. The mirror 44 reflects the transmitted beam through bundle 22 toward the detector 24, which comprises a plurality of detector elements for analyzing the cross sectional shape of the transmitted beam. The detector 24 is preferably a four quadrant (4Q) silicon diode detector, although any detector could be used that is capable of determining the amount of change in the cross sectional shape of the beam as a result of passing through the sample volume (e.g., a charge coupled detector). The 4Q detector 24 has two sets of opposing quadrants for receiving the transmitted beam, such as a north-south quadrant set and an east-west quadrant set. However, the optical axis of polarizer 18 must be aligned with either the north-south axis or the east-west axis of detector 24 for proper operation of monitor 10. Upon receiving the transmitted beam, detector 24 outputs a vertical signal representing the sum of the light received in the north-south quadrant and a horizontal signal representing the sum of the light received in the east-west quadrant.

Detection circuit 50 receives the vertical and horizontal signals from detector 24 and inputs them into summer 26 and differentiator 28. The resulting sum and difference signals may be converted from analog to digital signals by converters 30, 32 (as shown in FIG. 1). The difference between the vertical and horizontal signals indicates the degree of asymmetry, and the sum of the vertical and horizontal signals indicates the beam attenuation. Then, the sum and difference signals are forwarded to processor 34 where the difference signal is divided by the sum signal to produce an output signal at node 52 (FIG. 4) representing the profile value of the fluid. The circuit 50 transmits the output signal to the display 36.

Depending on the value of the output signal, an alarm signal may be triggered to actuate the alarm 38. For example, the alarm 38 may be actuated if either quality or intensity exceeds a preselected maximum value. Similarly, if the fluid level is below a preselected minimum level, an alarm signal is output to alarm 38.

The predefined cross sectional shape of the incident beam will determine the polarized shape of the transmitted beam. For example, if the incident beam has a circular profile, then the transmitted beam will be modified to have an elliptical profile. For monitoring fluid quality, it has been observed that the use (degradation) of fluids such as lubricating oils and cooking oils is proportional to the change in beam profile. This profile change is believed to be caused, at least in part, by increased Rayleigh-Brillouin scattering from larger hydrocarbon molecules produced during degradation. Thus, a higher level of degradation will produce a more elongated elliptical beam shape. Accordingly, the diameter of bundle 22 is greater than the diameter of strand 16 to accommodate transmission of the modified cross section of the beam.

Monitor 10 may be adapted for convenient insertion into a reservoir containing a fluid such that a sample volume of the fluid circulates within gap 42 to accommodate in situ evaluation of the fluid. To minimize false positive signals when the fluid level is below gap 42, the surfaces which define the gap are coated with a thin film of a transparent material which has a low surface energy and is not soluble in the fluid. The presently preferred coating material is Teflon AF-2400, a product of E. I. du Pont de Nemours and Company, although other transparent organic polymers might also be satisfactory. Alternatively, monitor 10 may be disposed in a fixed location so that fluid cells or other such samples are transported to the monitor for evaluation.

As various changes could be made in the above constructions and circuits without departing from the scope of the invention, it is intended that all matter contained in the above description and shown in the accompanying drawings shall be interpreted as illustrative and not in a limiting sense.

What is claimed is:

1. A device for monitoring the value of a parameter associated with a fluid, the device comprising:

a light source providing light;

a beam conditioner for conditioning the provided light into a beam having a predefined cross sectional shape, said beam conditioner being positioned to direct the beam of light through the fluid;

a detector being positioned for receiving the beam of light transmitted through the fluid and providing a shape signal representative of the cross sectional shape of the transmitted beam of light;

an optical polarizer for polarizing the beam of light; and a circuit for receiving the shape signal and determining the value of the fluid parameter by comparing the shape signal to the predefined cross sectional shape of the beam of light conditioned by the beam conditioner, said circuit providing an output signal indicative of the value of the fluid parameter.

2. The device of claim 1 wherein the light source comprises an LED.

3. The device of claim 1 wherein the beam conditioner comprises a lens.

4. The device of claim 3 wherein the beam conditioner further comprises an optical fiber for directing the beam through the fluid.

5. The device of claim 1 wherein the optical polarizer is disposed intermediate the light source and the fluid.

6. The device of claim 1 wherein the optical polarizer is disposed intermediate the fluid and the detector.

7. The device of claim 1 wherein one or more optical polarizers are disposed intermediate the light source and the detector.

8. The device of claim 1 further comprising a turning mirror for directing the transmitted beam toward the detector.

9. The device of claim 1 wherein the predefined cross sectional shape of the beam of light is circular.

10. The device of claim 1 wherein the detector comprises a plurality of detector elements for analyzing the cross sectional shape of the transmitted beam of light.

11. The device of claim 10 wherein the detector comprises a four quadrant detector having horizontal quadrants and vertical quadrants, wherein the polarizer is aligned with one of said horizontal quadrants and vertical quadrants, and wherein the shape signal comprises a vertical signal representative of an amount of light received in the vertical quadrants of the detector and a horizontal signal representative of an amount of light received in the horizontal quadrants of the detector.

12. The device of claim 11 wherein the circuit includes a summer for summing the vertical and horizontal signals, a differentiator for determining the difference between the vertical and horizontal signals and a processor for processing the sum and difference to indicate any change in shape of the beam.

13. The device of claim 11 wherein the circuit processes the vertical and horizontal signals to calculate the proportional distribution of light therebetween, which is compared to a predetermined reference value corresponding to the predefined cross sectional shape to indicate any change in the shape of the beam.

14. The device of claim 1 wherein the parameter associated with the fluid is quality.

15. The device of claim 1 wherein the parameter associated with the fluid is intensity.

16. The device of claim 1 wherein said device is adapted for in situ monitoring.

17. The device of claim 1 further comprising an alarm which is actuated when the output signal indicates the fluid parameter is above a predetermined value.

18. A device for detecting the level of a fluid in a reservoir comprising:
  a light source providing light;
  a beam conditioner for conditioning the provided light into a beam having a predefined cross sectional shape, said beam conditioner being positioned to direct the beam of light through a portion of the reservoir at a predetermined minimum level;
  a detector adapted to receive the beam of light transmitted through the reservoir and further adapted to provide a shape signal representative of the cross sectional shape of the transmitted beam of light; and
  a circuit for receiving the shape signal and determining the level of the fluid, said circuit providing a level signal indicative of the level of the fluid.

19. The device of claim 18 wherein said detector provides a first shape signal when the fluid level is at or above the predetermined minimum level and a second shape signal when the fluid level is below the predetermined minimum level.

20. The device of claim 18 wherein said detector provides a first shape signal when the fluid level is at or above the predetermined minimum level, a second shape signal when only a fluid meniscus is present at the predetermined minimum level, and a third shape signal representing the absence of any fluid at the predetermined minimum level.

21. The device of claim 18 wherein the beam conditioner comprises a lens and an optical fiber for directing the beam through the reservoir.

22. The device of claim 18 further comprising an optical polarizer for polarizing the beam of light.

23. The device of claim 22 wherein the detector comprises a four quadrant detector having horizontal quadrants and vertical quadrants, wherein the polarizer is aligned with one of said horizontal quadrants and vertical quadrants, and wherein the shape signal comprises a vertical signal representative of an amount of light received in the vertical quadrants of the detector and a horizontal signal representative of an amount of light received in the horizontal quadrants of the detector.

24. The device of claim 18 wherein the detector comprises a four quadrant detector and the circuit includes a processor for calculating the proportional distribution of light on the detector, which is compared to a predetermined reference value corresponding to the predefined cross sectional shape to indicate any change in the shape of the beam.

25. The device of claim 18 wherein said device is adapted for in situ monitoring.

26. The device of claim 18 further comprising an alarm which is actuated when the level signal indicates the fluid level is below the predetermined level.

27. A method for monitoring the value of a parameter associated with a fluid in a reservoir, the method comprising:
  providing light from a light source;
  conditioning the provided light into a beam having a predefined cross sectional shape;
  transmitting the beam through the reservoir at a predetermined level;
  detecting the transmitted beam of light;
  generating a shape signal representative of the cross sectional shape of the transmitted beam;
  analyzing the shape signal to determine the value of the fluid parameter; and
  generating an output signal indicative of the value of the fluid parameter.

28. The method of claim 27 wherein the fluid parameter is the level of the fluid within the reservoir.

29. The method of claim 27 further comprising the step of polarizing the beam.

30. The method of claim 29 wherein said polarizing step occurs prior to said transmitting step.

31. The method of claim 29 wherein said polarizing step occurs subsequent to said transmitting step and prior to said detecting step.

32. The method of claim 29 wherein the fluid parameter is the quality of the fluid.

33. The method of claim 31 wherein said analyzing step further comprises comparing the shape of the transmitted beam as represented by the shape signal to a predetermined reference value corresponding to the predefined cross sectional shape to indicate any change in the shape of the beam and thereby determine the amount of fluid degradation.

34. The method of claim 29 wherein the fluid parameter is the intensity of the fluid.

35. The method of claim 34 wherein said analyzing step further comprises comparing the shape of the transmitted beam as represented by the shape signal to a predetermined reference value corresponding to the predefined cross sectional shape to indicate any change in the shape of the beam and thereby determine the amount of fluid contamination.

* * * * *